United States Patent
Grüning et al.

Patent Number: 5,910,564
Date of Patent: Jun. 8, 1999

[54] POLYAMINO ACID ESTER COPOLYMERS

[75] Inventors: Burghard Grüning; Harald Rau; Jörg Simpelkamp; Christian Weitemeyer, all of Essen, Germany

[73] Assignee: Th. Goldschmidt AG, Essen, Germany

[21] Appl. No.: 08/761,637

[22] Filed: Dec. 6, 1996

[30] Foreign Application Priority Data

Dec. 7, 1995 [DE] Germany .............. 195 45 678

[51] Int. Cl.[6] .................................. C08G 69/08
[52] U.S. Cl. .................. 528/310; 528/328; 528/363; 525/419; 525/420
[58] Field of Search .................. 525/419, 420; 528/310, 328, 363

[56] References Cited

U.S. PATENT DOCUMENTS

| | | |
|---|---|---|
| 3,371,069 | 2/1968 | Miyamae et al. . |
| 3,819,588 | 6/1974 | Fujimoto et al. . |
| 4,450,150 | 5/1984 | Sidman . |
| 4,675,381 | 6/1987 | Bichon . |
| 5,118,784 | 6/1992 | Kubota et al. . |
| 5,219,952 | 6/1993 | Koskan et al. . |
| 5,292,858 | 3/1994 | Wood . |

FOREIGN PATENT DOCUMENTS

| | | |
|---|---|---|
| 0 578 448 A1 | 1/1994 | European Pat. Off. . |
| 0 578 449 A1 | 1/1994 | European Pat. Off. . |
| 2 253 190 | 5/1973 | Germany . |
| WO 92/14753 | 9/1992 | WIPO . |
| WO 94/01486 | 1/1994 | WIPO . |

OTHER PUBLICATIONS

M.B. Freeman, et al. "Biodegradability of Polycarboxylates: Structure Activity Studies", *Abstract of Papers of the ACS*.

*Primary Examiner*—Duc Truong
*Attorney, Agent, or Firm*—Scully, Scott, Murphy & Presser

[57] ABSTRACT

Copolymers derived from polyamino acids with at least 75% of the units present selected from the group consisting of structural units having the general formulas (I) and (II)

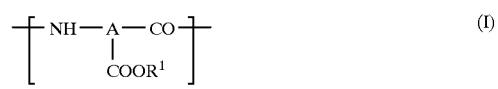

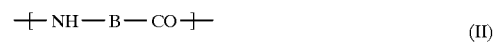

in which the structural elements A are identical or different trifunctional hydrocarbon radicals with 2 or 3 C atoms, wherein the copolymer contains at least three units of formula (I).

10 Claims, No Drawings

POLYAMINO ACID ESTER COPOLYMERS

BACKGROUND OF THE INVENTION

Polyamino acid derivatives, particularly polyaspartic acid, have aroused interest very recently because of their properties. One advantage of the polyaspartic acid skeleton is its very good environmental compatibility and biological degradability. The biological degradability of polymeric aspartic acids is a result of the basic structure, which is similar to a natural one and which has been derived from polyamino acids. The advantageous properties of polyaspartic acids with respect to the biological degradability in comparison to polymers with C-C skeletons (for example, polyacrylates) have been described (Abstracts of papers of the ACS, 1994, V208, 423–4; M. B. Freeman, Y. H. Paik, G. Swift, R. Wilczynski, S. K. Wolk, K. M. Yocom). The applications proposed are, primarily, use as biologically degradable complexing agents, softeners and detergent builders.

The immediate synthetic precursor in most cases is polysuccinimide, the cyclic imide of polyaspartic acid, or derivatives of monoethylenically unsaturated carboxylic acids, such as maleic acid.

EP-A-0578449 describes the synthesis of polysuccinimide by the heating of aspartic acid in polyalkylene glycols, alone or in a mixture with additional amino acids. WO 92/14753 describes the synthesis of polysuccinimide and polyaspartic acid by the thermal condensation of aspartic acid. U.S. Pat. No. 5,219,952 describes the synthesis of polysuccinimide from maleic acid anhydride and ammonia, and the hydrolysis of the product to form polyaspartic acid. EP-A-0578448 describes the synthesis of polysuccinimide by the heating of amino acids and monoethylenically unsaturated dicarboxylic acids or their ammonium salts.

These compounds present numerous advantageous properties, but they have no surface active properties. In order to obtain compounds which combine the positive properties of polyaspartic acid with surfactant properties, it is necessary to introduce hydrophobic, oil-compatible molecule parts into the predominantly hydrophilic polyaspartic acid skeleton.

The reaction of polysuccinimide with amines to form polyaspartic acid amides is also known in the state of the art (for example, DE-A-2253190). U.S. Pat. No. 5,292,858 describes the synthesis of copolymeric polyamino acid amides by the hydrolysis of polysuccinimide derivatives, prepared by reacting maleic acid semiesters with ammonia or amines.

In accordance with these teachings, copolymers with free carboxylic acid groups and alkylamide groups can be prepared. These copolymers however present serious drawbacks. Thus, as a result of the preparation, the products contain more or less small amounts of free alkylamines, which are undesired in many applications and whose use can also entail toxicological and ecological drawbacks. The alkylamines can additionally be released, for example, by hydrolytic cleavage, during the use of such copolymers.

BRIEF SUMMARY OF THE INVENTION

Copolymeric polyaspartic acid derivatives, in which a portion of the carboxyl groups are esterified with alcohols, particularly fatty alcohols, are not known so far. Such novel ester derivatives are made available by the invention: since the preparation of the compounds in accordance with the invention is not based on the use of amines, and since the copolymers also do not contain amines in bound form, the compounds in accordance with the invention do not present the above-mentioned drawbacks.

An additional advantage of the copolymers in accordance with the invention is their very good environmental compatibility, which is the result of the fundamental structure, which is close to the natural one, and derived from polyamino acids, and the linkage of the alkyl side chains by means of ester groups.

The copolymers in accordance with the invention can be adapted to a very great variety of application-technological requirements by the type and density of the alkyl side chains and by their molecular weights. Thus, short-chain alkyl-substituted derivatives can be suitable as sequestrants or they can be used in corrosion-protecting paints, particularly since they can be soluble in polar organic solvents.

Long-chain alkyl substituted copolymers present surface-active properties. By the variation of different parameters, such as chain length of the long-chain components, degree of polymerization of the copolymer, ratio of hydrophobic side chains to free carboxylic acid groups, etc., environmentally safe surfactants with excellent application properties can be obtained. They can be used in multiple applications, for example, as W/O or O/W emulsifiers. The foam-stabilizing properties allow an application as foam strengthener, for example, in mild cosmetic cleaning agents or in household detergents. Other fields of application of the surfactant materials with the ability to complex bivalent metal ions, such as $Ca^{2+}$, which is characteristic for polyaspartic acids, are detergent auxiliary agents and builders, dispersants and conditioners for cosmetic applications.

At least 75% of the units present in the copolymers in accordance with the invention consist of structural units selected from the group consisting of units having the general formulas (I) and (II)

in which each structural element A is the same or different and each is a trifunctional hydrocarbon radical with 2 or 3 C atoms, provided that a copolymer contains at least three units having the formula (I), in which $R^1$ can have the meaning of $R^2$, $R^3$ and $R^4$, where $R^2$ represents one or more residues selected from the group consisting of alkali metals, alkaline earth metals, hydrogen, and ammonium, i.e. $[NR^5R^6R^7R^8]^+$ where $R^5$–$R^8$ represent, independently of each other, hydrogen, alkyl or hydroxyalkyl, each preferably containing 1 to 4 carbon atoms, $R^3$ represents identical or different, straight or branched, saturated or unsaturated alkyl residues $R^9$ with 6–24 C atoms or radicals having the structure —X—$R^9$, where X represents an oligo- or polyoxyalkylene chain with 1–100 oxyalkylene units, $R^4$ represents identical or different, straight or branched, saturated or unsaturated alkyl residues with 1–5 C atoms, and in each case at least one residue $R^1$ must have the meaning of $R^2$ and at least one residue $R^1$ must have the meaning of $R^3$ or $R^4$, and the units [—NH—B—CO] are residues selected from the group consisting of protein-forming and nonprotein-forming amino acids, and constitute not more than 20 wt. % of the copolymer.

The copolymer is terminated on the terminal nitrogen seen in formulas (I) and (II) with —H or with the acyl residue of, e.g., maleic, fumaric, or succinic acid or of a salt or monoester thereof with an $R^2$, $R^3$ or $R^4$ group. The copolymer is terminated at the terminal carboxyl group seen in formulas (I) and (II) —$OR^1$, with —OH or —$NH_2$. As will be seen below, in a preferred form the copolymer is comprised between the aforementioned terminal nitrogen and carboxyl groups entirely of units of the formulas (I) and (II).

DETAILED DESCRIPTION OF THE INVENTION

Amino acid components [—NH—B—CO] from the group of protein-forming amino acids which can be used include, for example, residues of glutamine, asparagine, lysine, alanine, glycine, tyrosine, tryptophan, serine and cysteine as well as their derivatives; the nonprotein-forming amino acid residues can be, for example, residues of β-alanine, ω-amino-1-alkanoic acids, etc.

Compounds in accordance with the invention include those which contain at least one free carboxylate group ($R^1$ is H, metal such as alkali metal, or ammonium), a residue $R^4$ from the group of straight or branched chain, saturated or unsaturated alkyl residues with 1–5 C atoms (for example, methyl, ethyl, n-propyl, i-propyl, n-butyl, i-butyl, s-butyl, n-pentyl) and a residue $R^3$, identical or different radicals with the structure $R^9$—X—, where $R^9$ originates from the group of straight or branched, saturated or unsaturated alkyl residues with 6–24 C atoms (for example, branched or linear octyl, decyl, dodecyl, tetradecyl, hexadecyl, octadecyl, docosyl residues, and also unsaturated or polyunsaturated species such as, for example, oleyl) and X, a polyoxyalkylene chain of 0–100 alkylene glycol units, is preferably derived from ethylene oxide, propylene oxide or mixtures thereof. A preferred form of the copolymer in accordance with the invention contains alkyl residues $R^{10}$ with 8–24 C atoms without alkylene glycol spacer (alkylene glycol chain length=0).

It is particularly advantageous to use copolymers in accordance with the invention which are compounds derived from polyaspartic acid, where A is a trifunctional radical with 2 C atoms having the structure (A1) or (A2)

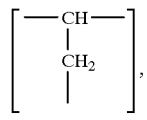

(A1)

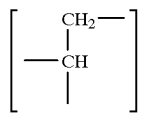

(A2)

The manufacture of the copolymers can be carried out by the sequential reaction of polyaspartic acid imide (polysuccinimide, prepared, for example, in accordance with U.S. Pat. No. 5,219,952) with alcohols $R^4OH$ in a first step and, should the situation arise, following with partial reaction with alcohols $R^3OH$. Here $R^3$ and $R^4$ have the above-indicated meanings. It is preferred that $R^4$ is a straight or branched alkyl residue with 1–4 C atoms. Preferably $R^3$ is a straight or branched, saturated or unsaturated alkyl residue with 8–24 C atoms. If polyoxyalkylene chains X are to be present, they are preferably derived from ethylene oxide, propylene oxide or mixtures thereof. In a third step, the ester groups derived from $R^4OH$ can be partially or completely hydrolyzed under mild conditions, with the release of the carboxylic acid or carboxylic groups which are characteristic for the copolymers in accordance with the invention. In this process, the ester groups of the long chain alcohols, which continue to characterize the copolymers in accordance with the invention, preferably remain intact.

As alcohols with formula $R^4OH$, it is possible to use, for example, compounds with $R^4$=methyl, ethyl, n-propyl, i-propyl, n-butyl, i-butyl, s-butyl and n-pentyl. Methyl and ethyl alcohol are used particularly preferably.

As the residue $R^3$ it is possible to use, for example, linear or branched decyl, dodecyl, tetradecyl, hexadecyl, octadecyl, docosyl residues or unsaturated alkyl residues such as oleyl.

A preferred method consists of reacting the aspartic acid imide with an excess of the alcohol at 1–20 bar and 65–200° C. for 6–48 h, with or without the addition of additional solvent, such as dimethyl sulfoxide, dimethylformamide, ethylene glycol, oligoethylene glycol, mono- and oligoethylene glycol alkyl ether with or without the presence of an acidic or basic catalyst, preferably a mineral acid, organic acids, acidic ion exchangers, alkali or alkaline earth salts of organic or mineral acids, alkali and alkaline earth hydroxides, alkoxylates, particularly preferably alkali or alkaline earth alkoxylates of the alcohols used.

An additional method for the preparation of the copolymers in accordance with the invention is characterized in that one or more monoesters of monoethylenically unsaturated dicarboxylic acids is reacted with ammonia or the ammonium salts of these acids are thermally transformed into the polymer. It is possible to use derivatives of maleic acid, fumaric acid, itaconic acid, alkenylsuccinic acid, alkylmaleic acid, citraconic acid or their ammonium salts, preferably derivatives of maleic acid, fumaric acid or itaconic acid, and particularly preferably maleic acid derivatives having the formulas (III) and (IV)

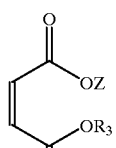

(III)

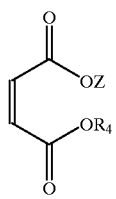

(IV)

where Z denotes hydrogen and/or ammonium, and $R^3$ and $R^4$ denote the above-mentioned residues. These maleic acid derivatives can in each case be used separately or in a mixture.

Preferably used residues $R^3$ are alkyl residues with 8–24 C atoms without a polyalkylene glycol portion, for example, linear or branched decyl, dodecyl, tetradecyl, hexadecyl, octadecyl or docosyl residues as well as unsaturated alkyl residues, such as, for example, oleyl. Residues $R^4$ which are preferably used are alkyl residues with 1–4 C atoms without a polyalkylene glycol portion, preferably methyl, ethyl, n-propyl, i-propyl, n-butyl, i-butyl, or b-butyl. The ratio of components (III) and (IV) is preferably between 100:0 and 10:90, particularly preferably between 75:25 and 25:75.

In the method in accordance with the invention, the maleic acid monoesters are reacted with 0.5–1.5, preferably 0.8–1.5, equivalents of ammonia (as ammonia gas or solution). The reaction can be conducted with or without the addition of an organic solvent. Possible solvents are alcohols, ethers, oligo- and poly(alkylene) glycols or glycol ethers, dimethyl sulfoxide and dimethylformamide. If a solvent is used, it is preferred to use a short-chain alcohol $R^4OH$. The reaction takes place at temperatures of 0–150° C., preferably 40–120° C. A preferred process consists, for example, of the reaction of maleic acid monoalkyl ester and aqueous or gaseous ammonia at 50–70° C., removal of any water originating from the ammonia solution or the reaction water at a reduced pressure and 20–120° C., preferably 50–80° C., and, still at reduced pressure, at a slowly increasing temperature up to 90–150° C., preferably 100–120° C., with stirring of the reaction mixture, which becomes increasingly viscous. During this time, the conversion to copolymer takes place. Under the reaction conditions, a portion of the ester groups, preferably those derived from $R^4OH$, is simultaneously hydrolyzed and the desired carboxylic acid or carboxylate groups are released. Under the reaction conditions, the formation of cyclic imide structures (V) from the hydrolyzed aspartic acid units (VI) occurs to only a secondary degree.

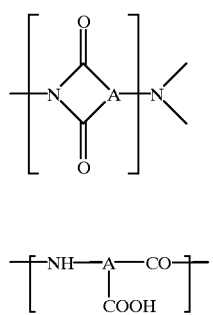

In addition, it can be assumed that imide structures (V) present in the product are additionally opened under the application conditions in the presence of an aqueous medium with release of the acid units (VI).

By a mild partial or complete hydrolysis, preferably of the ester functions derived from the short-chain alcohol $R^4OH$, if desired, the proportion of free acid groups or carboxylate groups can be further increased. For the hydrolysis, solutions or suspensions of the copolymer in organic solvents are reacted with water or steam, or the copolymers are hydrolyzed in water with or without the addition of organic cosolvents. This reaction can take place without catalyst or in the presence of organic or mineral acids, acidic ion exchangers or acidic minerals or basic compounds such as metal hydroxides or amines. It is preferred to use as bases alkali metal hydroxides or alkaline earth metal hydroxides, for example, sodium hydroxide and potassium hydroxide, in catalytic or stoichiometric quantities.

By the addition of amino and carboxy functional compounds to the reaction mixture, copolymers can be obtained in which the available units are bound by amide bonds. Suitable compounds are polyamino acids from the group of the 20 protein-forming amino acids, which are contained as monomers in all natural proteins, in pure enantiomeric or racemic form, such as, for example, glutamine, asparagine, lysine, alanine, glycine, tyrosine, tryptophan, serine and cysteine as well as their derivatives, or nonprotein-forming amino acids with, in each case, one or more amino or carboxy functions such as, for example, β-alanine or ω-amino-1 alkanoic acids. The components, preferably 0–20 wt. %, are added to the starting mixture of the maleic acid derivatives or they are reacted for the modification of the chain ends after complete synthesis of the polymer with the polymer, preferably with the addition of polar solvents, such as, for example, alcohols or dimethylformamide.

The copolymers in accordance with the invention present excellent properties as sequestrant, as additives to colors or lacquers and, particularly, in the stabilization of O/W or W/O emulsions and as foam stabilizers. Because of their structure which is derived from polyamino acids, they present a high environmental compatibility.

Examples of copolymers in accordance with the invention are:

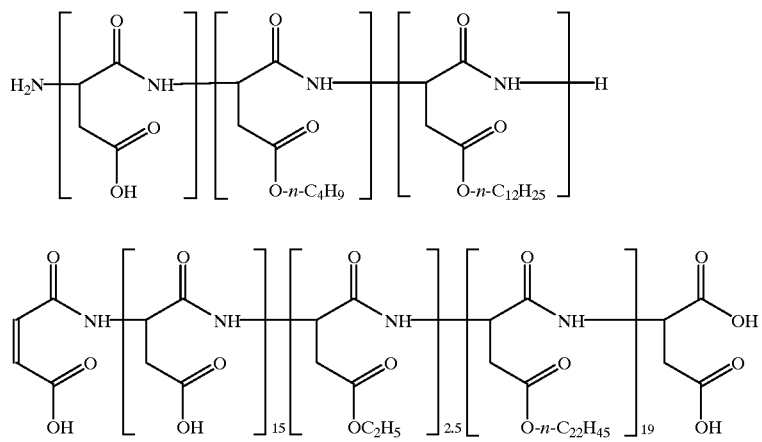

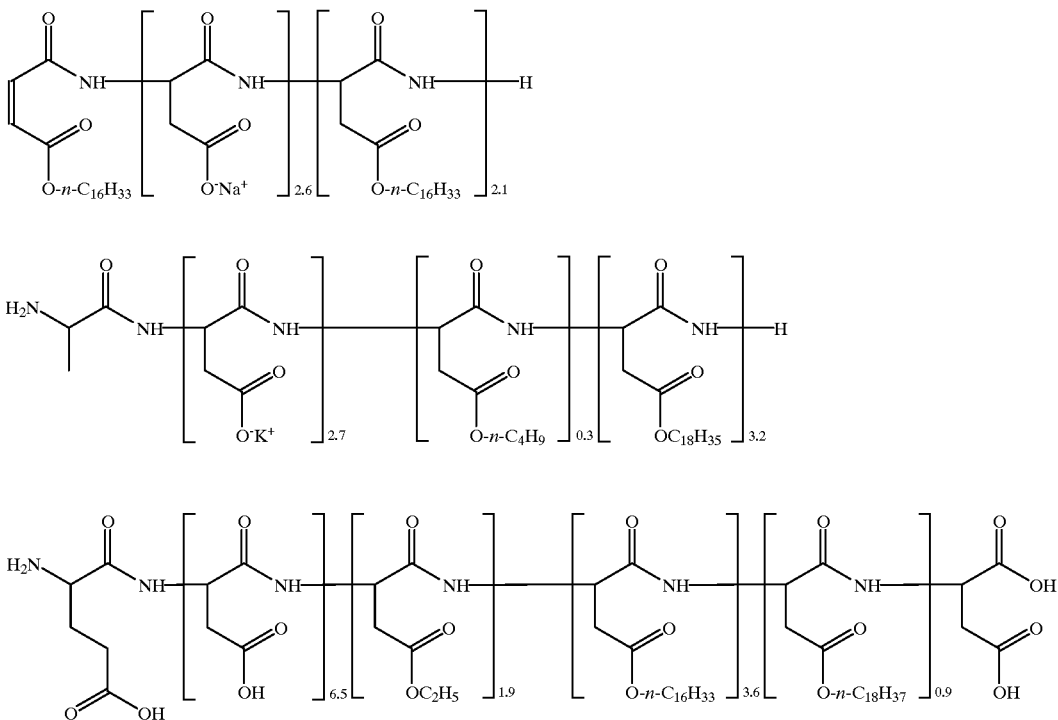

For simplification, all the structures given as examples are shown with the α-linkage (VII); this does not represent a statement of the actual ratio of α/β structures in the polymers in accordance with the invention.

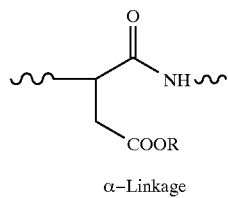

α–Linkage

VII

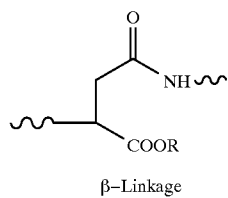

β–Linkage

VIII

EXAMPLE 1

In a 200-mL flask with an agitator producing high shear forces, a thermometer and a distillation attachment, 710 g maleic acid monododecyl ester (2.5 mol), 360 g maleic acid monoethyl ester (2.5 mol) and 100 mL n-butanol were heated to 50° C. Over 20 min, 340 g 25% aqueous ammonia solution (5 mol) was added dropwise at a maximum temperature of 70° C. After a reaction time of 30 min, with slow pressure reduction to 30 mbar and at a maximum temperature of 80° C., water and butanol were separated by distillation over 2 h. As soon as no water visibly condensed in the condenser, the preparation was slowly heated to 110° C. under a vacuum within 6 h. Then a yellow-brown, caramel-like composition was obtained. Analysis by $^{13}$C-NMR showed the composition was a partially esterified polyaspartic acid, with a ratio of —COOH:—COOC$_{12}$H$_{25}$ of approximately 1:1. The ethyl ester and the dodecyl alcohol portion were less than 1 mol %. The gel chromatogram, measured in a solution of tetrahydrofuran, showed an average molecular weight of approximately 900 (corresponding to a chain length of N=approximately 4.5; calibration against polystyrene).

EXAMPLE 2

500 g of the product of Example 1 was heated in an evacuable kneader heated to 100° C. and heated slowly to 120° C. within 6 h at 30 mbar. The resulting product had a mean molecular weight of approximately 2400 (N=approximately 12) as shown by GPC.

EXAMPLE 3

As described in Example 1, 422 g of maleic acid monostearyl ester (1.2 mol), 826 g maleic acid monobutyl ester (4.8 mol), 100 mL n-butanol and 408 g 25% ammonia solution (6 mol) were reacted. The resulting solid, slightly tacky product showed by $^{13}$C-NMR a ratio of the groups —COOH:—COOC$_4$H$_9$:—COOC$_{18}$H$_{37}$ of approximately 750 (N=approximately 4.3).

EXAMPLE 4

500 g of the product of Example 3 was further processed as described under Example 2 to increase the molecular weight. The resulting solid product had a mean molecular weight of approximately 2000 (N=approximately 11.5) as shown by GPC.

EXAMPLE 5

As described in Example 1, 1098 g maleic acid monooleyl ester (3 mol), 316 g itaconic acid monoethyl ester (2 mol)

and 100 mL n-butanol were reacted with 340 g 25% ammonia solution (5 mol). The resulting highly viscous product showed by $^{13}$C-NMR a ratio of —COOH:—COOC$_{18}$H$_{35}$ of approximately 0.7:1. GPC showed a mean molecular weight of approximately 1100 (N=approximately 4.1).

EXAMPLE 6

485 g polyaspartic acid imide (mean MW 1500), 800 g methanol and 17.8 g sodium methylate were heated to 170° C. in a pressure apparatus at 18 bar. These conditions were maintained for over 8 h. After cooling, the residue (35 g) was separated by filtration, and the excess methanol was separated by distillation at 100° C. and 30 mbar. GPC of the remaining residue showed a mean molecular weight of approximately 1400. The degree of esterification was 78% as shown by $^{13}$C-NMR. The product was dissolved in 2000 g dimethylformamide. In a 400-mL apparatus with agitator, thermometer, column, reflux condenser and cold trap, 535 g oleyl alcohol and 9 g tetraisopropyl titanate were added under nitrogen to the solution of the product. The preparation was heated (approximately 125° C.) at approximately 300 mbar until reflux of the dimethylformamide was obtained. The performance of the column was adjusted in such a manner that only methanol condensed in the cold trap. After 5 h reaction time, the column was separated and the dimethylformamide was removed by distillation at 30 mbar. $^{13}$C-NMR showed a transesterification degree of 88% of the theoretical. The product was heated with 400 g water and 5 g sodium hydroxide for 1 h at 60° C. and then, for the conversion to the salt, was converted into the free acid by means of a column with a highly acidic ion exchanger (LEWATIT SPC 108, Bayer AG). Then the water and the methanol produced were drawn off in a rotary evaporator at approximately 30 mbar. The resulting product had a —COOH:—COOC$_{18}$H$_{35}$ ratio of approximately 1:0.8 and a mean molecular weight of 1200 (N=approximately 5.3).

EXAMPLE 7

485 g polyaspartic acid imide (mean MW 1500), 1480 g n-butanol and 31.1 g sodium n-butyrate were heated to 180° C. in a pressure apparatus at 5 bar for 10 h. After cooling, the mixture was filtered and excess n-butanol was removed by distillation to 100° C. and 30 mbar. GPC of the remaining residue showed a mean MW of approximately 1200. The degree of esterification was 69% as shown by $^{13}$C-NMR.

EXAMPLE 8

As described in Example 1, 710 g maleic acid monododecyl ester (2.5 mol), 860 g maleic acid monobutyl ester (5.0 mol), 300 mL n-butanol and 510 g 25% ammonia solution (7.5 mol) and 36 g (0.4 mol) DL-alanine were reacted. The resulting, slightly tacky product showed by 13C-NMR a ratio of the groups —COOH:—COOC$_4$H$_9$:—COOC$_{12}$H$_{25}$:Ala of approximately 1.6:0.5:1.0:1.5. GPC showed a mean molecular weight of approximately 645 (N=approximately 3.7).

EXAMPLES 9 TO 12

Using the products of Examples 1,3,5 and 6, the following preparation with sodium lauryl ether sulfate solution (28% in water, subsequently called NaLES) were prepared:

| Example | Product of Example | Amount (g) of Product | Amount (g) of 0.1M NaOH solution | Amount (g) of NaLES | Water (g) |
|---|---|---|---|---|---|
| 9 | 1 | 10 | 23 | 40 | 0 |
| 10 | 3 | 10 | 0 | 40 | 23 |
| 11 | 5 | 10 | 0 | 40 | 23 |
| 12 | 6 | 10 | 11 | 40 | 12 |

0.07 g of each preparation was dissolved separately in 200 mL water. For comparison, 0.1 g of a preparation of 40 g NaLES and 31.2 g of an acylated protein hydrolysate solution were dissolved in 200 mL. In a 1000-mL graduated cylinder these solutions were agitated to generate foam, using a turbine. Then the decrease in the volume of the foam was observed. The results are presented in the following table (values in mL):

| Time after turbine shutoff | Ex. 9 | Ex. 10 | Ex. 11 | Ex. 12 | Comparison example |
|---|---|---|---|---|---|
| Immediately | 160 | 200 | 170 | 180 | 150 |
| 30 Min. | 150 | 180 | 160 | 170 | 120 |
| 60 Min. | 140 | 180 | 160 | 170 | 120 |
| 3 Hrs. | 130 | 160 | 150 | 160 | 110 |
| 6 Hrs. | 120 | 150 | 130 | 150 | 100 |
| 24 Hrs. | 100 | 120 | 100 | 110 | 70 |

EXAMPLE 13

7.5 g of the product Example 2 was dissolved at 50° C. in 67.5 g of low viscosity paraffin oil (5° Engler). In an agitator set at high speed, 75.0 g water was added. An O/W emulsion was obtained which remained stable over a test period of 3 weeks.

EXAMPLE 14

15.0 g of the product of Example 4 was stirred with 100.0 g water. During this time, the pH value was adjusted to 7 by the slow addition of 29 mL diluted NaOH (0.1 mol/L). 114 g paraffin oil (5° Engler) was added to the resulting slightly turbid solution in a high-speed agitator. The resulting W/O emulsion was still stable after 2 weeks.

EXAMPLE 15

Example 13 was repeated except for using isopropyl myristate instead of paraffin oil. The resulting O/W emulsion was still stable after 3 weeks.

We claim:

1. A copolymer derived from polyaspartic acids, wherein at least 75% of the units present are selected from the group consisting of structural units having the general formula (I) and (II)

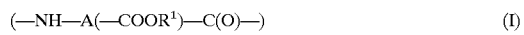
(—NH—A(—COOR$^1$)—C(O)—)  (I)

(—NH—B—C(O)—)  (II)

in which each structural element A is the same or different and each is a trifunctional hydrocarbon radical with 2 C atoms having the structure (A1) or (A2),

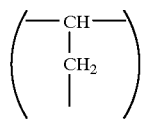

(A1)

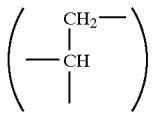

(A2)

wherein said copolymer contains at least three units having said formula (I), in which each $R^1$ can have the meaning of $R^2$, $R^3$ or $R^4$, where $R^2$ represents one or more residues selected from the group consisting of alkali metals, alkaline earth metals, hydrogen, and ammonium of the formula $(NR^5R^6R^7R^8)^+$, where $R^5$–$R^8$ represent, independently of each other, hydrogen, alkyl or hydroxyalkyl, $R^3$ represents identical or different, straight or branched, saturated or unsaturated alkyl residues $R^9$ with 6–24 C atoms or radicals having the structure —X—$R^9$, where X represents an oligo- or polyoxyalkylene chain with 1–100 oxyalkylene units, $R^4$ represents identical or different, straight or branched, saturated or unsaturated alkyl residues with 1–5 C atoms, and in each case at least one residue $R^1$ must have the meaning of $R^2$ and at least one residue $R^1$ must have the meaning of $R^3$ or $R^4$; and each unit (—NH—B—C(O)—) is a residue selected from the group consisting of protein-forming and nonprotein-forming amino acids, and the units (—NH—B—C(O)—) constitute not more than 20 wt %. of the copolymer.

2. A copolymer in accordance with claim 1, in which at least one residue $R^1$ has the meaning of $R^2$ and at least one residue $R^1$ has the meaning of $R^4$.

3. A copolymer in accordance with claim 1, in which at least one residue $R^1$ has the meaning of $R^2$ and at least one residue $R^1$ has the meaning of $R^3$.

4. A copolymer in accordance with claim 1, in which at least one residue $R^1$ has the meaning of $R^2$ and at least one residue $R^1$ has the meaning of $R^3$ and at least one residue $R^1$ has the meaning of $R^4$.

5. A copolymer in accordance with claim 1 in which each $R^3$ is identical or different and each is a straight or branched, saturated or unsaturated alkyl residue $R^{10}$ with 8–24 C atoms.

6. A copolymer in accordance with claim 3 in which each $R^3$ is identical or different and each is a straight or branched, saturated or unsaturated alkyl residue $R^{10}$ with 8–24 C atoms.

7. A copolymer in accordance with claim 4 in which each $R^3$ is identical or different and each is a straight or branched, saturated or unsaturated alkyl residue $R^{10}$ with 8–24 C atoms.

8. A surfactant-containing preparation comprising a copolymer in accordance with claim 1.

9. A composition selected from the group consisting of emulsifiers, foam strengtheners, detergent auxiliary substances, complexing agents for polyvalent cations, dispersing aids and conditioners and comprising a copolymer in accordance with claim 1.

10. A surfactant or foam strengthener useful in a cleaning agent or cosmetic preparation and comprising a copolymer in accordance with claim 1.

* * * * *